(12) United States Patent
Sih et al.

(10) Patent No.: US 7,937,147 B2
(45) Date of Patent: May 3, 2011

(54) HIGH FREQUENCY STIMULATION FOR TREATMENT OF ATRIAL FIBRILLATION

(75) Inventors: Haris Sih, Minneapolis, MN (US); Mark Schwartz, White Bear Lake, MN (US); Anthony V. Caparso, St. Louis Park, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 491 days.

(21) Appl. No.: 11/680,322

(22) Filed: Feb. 28, 2007

(65) Prior Publication Data

US 2008/0208271 A1 Aug. 28, 2008

(51) Int. Cl.
*A61N 1/36* (2006.01)
(52) U.S. Cl. ............................................. 607/5
(58) Field of Classification Search ..................... 607/5
See application file for complete search history.

(56) References Cited

U.S. PATENT DOCUMENTS

| | | | | |
|---|---|---|---|---|
| 4,649,936 A | * | 3/1987 | Ungar et al. | 607/118 |
| 5,243,980 A | | 9/1993 | Mehra | |
| 5,951,593 A | * | 9/1999 | Lu et al. | 607/14 |
| 6,431,173 B1 | * | 8/2002 | Hoffmann | 128/898 |
| 6,928,325 B2 | | 8/2005 | Zhu et al. | |
| 7,081,130 B2 | | 7/2006 | Jang | |
| 7,190,998 B2 | * | 3/2007 | Shalev et al. | 607/3 |
| 2004/0010303 A1 | | 1/2004 | Bolea et al. | |
| 2005/0187586 A1 | | 8/2005 | David et al. | |
| 2006/0206154 A1 | * | 9/2006 | Moffitt et al. | 607/9 |
| 2006/0265038 A1 | | 11/2006 | Hagen et al. | |

OTHER PUBLICATIONS

Deisenhofer et al. Cather Ablation of Atrial Fibrillation. Catheter Ablation of Cardiac Arrhythmias. Pub: Steinkopff (2006) 211-246.*
Po, Sunny S., et al., "Rapid and Stable Re-Entry Within the Pulmonary Vein as a Mechanism Initiation Paroxysmal Atrial Fibrillation.", *J. Am. Coll. Cardiol.*, (2005),45:1871-1877.
Patterson, E et al., "Triggered Firing in Pulmonary Veins Initiated by in vitro Autonomic Nerve Stimulation", *Heart Rhythm*, (2005),2:624-631.
Po, Sunny S., et al., "Experimental Model for Paroxysmal Atrial Fibrillation Arising at the Pulmonary Vein-Atrial Junctions.", *Heart Rhythm*, (2006),3:201-208.
Levy, S "Characterization of Different Subsets of Atrial Fibrillation in General Practice in France: the ALFA study. The College of French Cardiologists.", *Circulation*, (1999),99:3028-3035.

(Continued)

*Primary Examiner* — Carl H Layno
*Assistant Examiner* — Jeremiah T Kimball
(74) *Attorney, Agent, or Firm* — Pauly, DeVries, Smith & Deffner, L.L.C.

(57) ABSTRACT

The invention relates to methods and devices for treating and/or preventing atrial fibrillation. In an embodiment, the invention includes a method of treating and/or preventing atrial fibrillation including applying an oscillating electrical stimulus to a tissue of a patient, the oscillating electrical stimulus sufficient to block transmission of electrical signals through the tissue. In an embodiment, the invention includes an implantable medical device including a stimulator configured to generate an oscillating electrical stimulus at a frequency and amplitude sufficient to block transmission of electrical signals through a tissue, a stimulation electrode in communication with the stimulator, the stimulation electrode configured to deliver the oscillating electrical stimulus to the tissue, and control circuitry in communication with the stimulator, the control circuitry configured to selectively deliver the oscillating electrical stimulus to treat and/or prevent atrial fibrillation. Other embodiments are also described herein.

20 Claims, 10 Drawing Sheets

OTHER PUBLICATIONS

Oh, S "Vagal Denervation and Atrial Fibrillation Inducibility: Epicardial Fat Pad Ablation does not have Long-Term Effects.", *Heart Rhythm*, (2006),3:701-708.

Armour, Andrew J., et al., "Gross and Microscopic Anatomy of the Human Intrinsic Cardiac Nervous System", *Anatomical Record*, (1997),247:289-298.

Haissaguerre, Michel et al., "Spontaneous Initiation of Atrial Fibrillation by Ectopic Beats Origination in the Pulmonary Veins", *NEJM*, (2006),339:659-666.

Haissaguerre, Michel et al., "Pulmonary Veins in the Substrate for Atrial Fibrillation", *J. Am. Coll. Cardio.*, (2004),43:2290-2292.

Balkhy, Husam H., et al., "Autonomic Ganglionated Plexi: Characterization and Effect of Epicardial Microwave Ablation in Canine Model of Vagally Induced Acute Atrial Fibrillation", *Meeting for the International Society for Minimally Invasive Cardiothoracic Surgery* (Abstract), (2006).

Kilgore, K. L., et al., "Nerve Conduction Block Utilising High-Frequency Alternation Current", *Med. Biol. Eng. Comput.*, (2004),42:394-406.

Kumagai, Koichiro et al., "Electrophysiologic Properties of Pulmonary Veins Assessed Using a Multielectrode Basket Catheter", *J. Am. Coll. Cardio.*, (2004),43:2281-2289.

Nathan, H et al., "The Junction Between the Left Atrium and the Pulmonary Veins: An Anatomic Study of Human Hearts", *Circulation*, (1966),34:412-422.

Randall, David C., et al., "Ablation of Posterior Atrial Ganglionated Plexus Potentiates Sympathetic Tachycardia to Behavioral Stress", *Am. J. Physiol. Regulatory Integrative Comp. Physiol.*, (1998),275:779-787.

Verrier, Richard L., et al., "Autonomic Aspects of Arrhytmogenesis: The Enduring and the New", *Curr. Opin. Cardiol.*, (2004),19(1):2-11.

Dilling-Boer, Dagmara et al., "Ablation of Focally Induced Atrial Fibrillation: Selective or Extensive?", *J. Cardio. Electyphys.*, (2004),15:200-205.

Scherlag, Benjamin J., et al., "Autonomically Induced Conversion of Pulmonary Vein Focal Firing Into Atrial Fibrillation", *J. Am. Coll. Cardiol.*, (2005),45:1878-1886.

Scherlag, Benjamin J., et al., "Electrical Stimulation to Identify Neural Elements on the Heart: Their Role in Atrial Fibrillation", *J. Interv. Card. Electrophysiol*, (2005),13 Supp. 1:37-42.

Schauerte, Patrick "Focal Atrial Fibrillation: Experimental Evidence for a Pathophysiologic Role of the Autonomic Nervous System", *Cardiovasc. Electrophysiol.*, (2001),12:592-599.

Schauerte, Patrick et al., "Catheter Ablation of Cardiac Autonomic Nerves for Prevention of Vagal Atrial Fibrillation", *Circulation*, (2000),102:2774-2780.

Patterson, Eugene et al., "Sodium-Calcium Exchange Initiated by the $Ca^{2+}$ Transient: An Arrhythmia Trigger Within Pulmonary Veins", *J. Am. Coll. Cardiol.*, (2006),47:1196-1206.

Chevalier, P "Quantitative Study of Nerves of the Human Left Atrium", *Heart Rhythm*, (2005),2:518-522.

Pappone, Carlo "Pulmonary Vein Denervation Enhances Long-Term Benefit After Circumferential Ablation for Paroxysmal Atrial Fibrillation", *Circulation*, (2004),109:327-334.

Tai, C "Simulation Analysis of Conduction Block in Unmyelinated Axons Induced by High-Frequency Biphasic Electrical Currents", *IEEE T-BME*, (2005),52:1323.

Schauerte, P et al., "Ventricular Rate Control during Atrial Fibrillation by Cardiac Parasympathetic Nerve Stimulation: A Transvenous Approach.", *J. Am. Coll. Cardiol.*, (1999),34(7):2043-2050.

Oral, Hakan et al., "Pulmonary Vein Isolation for Paroxysmal and Persistent Atrial Fibrillation.", *Circulation*, (2002),105:1077.

* cited by examiner

HIGH FREQUENCY STIMULATION FOR TREATMENT OF ATRIAL FIBRILLATION

FIELD OF THE INVENTION

The invention relates to devices and methods for the control of atrial fibrillation. More particularly, the invention relates to implantable medical devices and methods for treating and/or preventing atrial fibrillation.

BACKGROUND OF THE INVENTION

Atrial fibrillation is a condition wherein the upper chambers of the heart, called the atria, flutter or quiver rapidly. By some estimates, 1 in 20 people over the age of 65 experience atrial fibrillation. During atrial fibrillation, the contractions of the atria are not coordinated with the contractions of the ventricles. This can result in improper filling of the ventricles and inefficient operation of the heart. Individuals suffering from atrial fibrillation may experience palpitations, dizziness, fainting, weakness, fatigue, shortness of breath, and angina. In addition to causing discomfort for patients and potentially limiting physical activity, atrial fibrillation can cause very serious complications. For example, atrial fibrillation allows blood to stagnate inside of the heart, which can lead to the formation of blood clots. Blood clots in the vasculature are dangerous and can result in substantial morbidity and mortality. For example, a blood clot can result in a myocardial infarction if lodged in the coronary artery or a stroke if lodged in an artery that supplies blood to the brain. Blood clots that follow from atrial fibrillation are believed to account of at least one-third of stroke incidence in patients over 85 years of age. For these reasons, is important to provide effective medical treatment for atrial fibrillation.

Various therapeutic approaches currently exist for treating atrial fibrillation, including the administration of drugs for ventricular rate control and drugs for atrial rhythm control. Such drugs can include digoxin, beta adrenoceptor blockers (such as atenolol, metoprolol, and propranolol), amiodarone, disopyramide, calcium channel antagonists (verapamil, diltiazam), sotalol, flecainide, procainamide, quinidine, and propafenone, among others. However, the use of drugs is not always effective and can result in undesirable side effects.

Another approach for treating atrial fibrillation involves the ablation of tissues on or near the heart. Ablation is a process of physically destroying tissue. Ablation of tissue prevents the destroyed tissue from initiating and/or conveying inappropriate excitatory depolarization waves. Ablation techniques to control atrial fibrillation generally involve applying radiofrequency (RF), microwave, ultrasound, laser, or other energy to certain tissue, or by freezing (usually through a catheter) certain tissue on or near the heart. Ablation results in a small scar that is electrically inactive and incapable of generating or propagating inappropriate electrical signals. The electrical abnormalities associated with atrial fibrillation are often generalized across the tissue of the atria. Therefore, control of atrial fibrillation through ablation often includes forming a series of scars across the atria, rather than just in one localized area. Techniques such as the MiniMaze or Cox Maze procedures involve creating a pattern of atrial lesions or scars to control the propagation of inappropriate electrical signals.

However, there are significant drawbacks associated with tissue ablation. One drawback is that ablation can be a lengthy procedure and exposes the patient to a risk of stroke. There is also a risk of causing unintentional damage to surrounding tissue during an ablation procedure. Finally, tissue ablation is non-reversible, and the long-term side-effects are poorly understood.

Improved methods for treating atrial fibrillation and related devices are needed.

SUMMARY OF THE INVENTION

The invention relates to methods and devices for treating and/or preventing atrial fibrillation. In an embodiment, the invention includes a method of treating and/or preventing atrial fibrillation including applying an oscillating electrical stimulus to a tissue of a patient, where the oscillating electrical stimulus is sufficient to block transmission of electrical signals through the tissue.

In an embodiment, the invention includes an implantable medical device including a stimulator that is configured to generate an oscillating electrical stimulus at a frequency and an amplitude that is sufficient to block transmission of electrical signals through a tissue. The implantable device further includes a stimulation electrode in communication with the stimulator, where the stimulation electrode is configured to deliver the oscillating electrical stimulus to the tissue, and control circuitry in communication with the stimulator, where the control circuitry is configured to selectively deliver the oscillating electrical stimulus to treat and/or prevent atrial fibrillation.

In an embodiment, the invention includes an implantable medical device including a pulse generator that is configured to generate pacing pulses, a pacing electrode that is in communication with the pulse generator, a stimulator that is configured to generate an oscillating electrical stimulus at a frequency and amplitude sufficient to block transmission of electrical signals through a tissue, a stimulation electrode in communication with the stimulator, where the stimulation electrode is configured to deliver the oscillating electrical stimulus to the tissue, and control circuitry in communication with the stimulator and the pulse generator, the control circuitry configured to control delivery of the pacing pulses and the oscillating electrical stimulus.

The invention may be more completely understood by considering the detailed description of various embodiments of the invention that follows in connection with the accompanying drawings.

Figure 1:
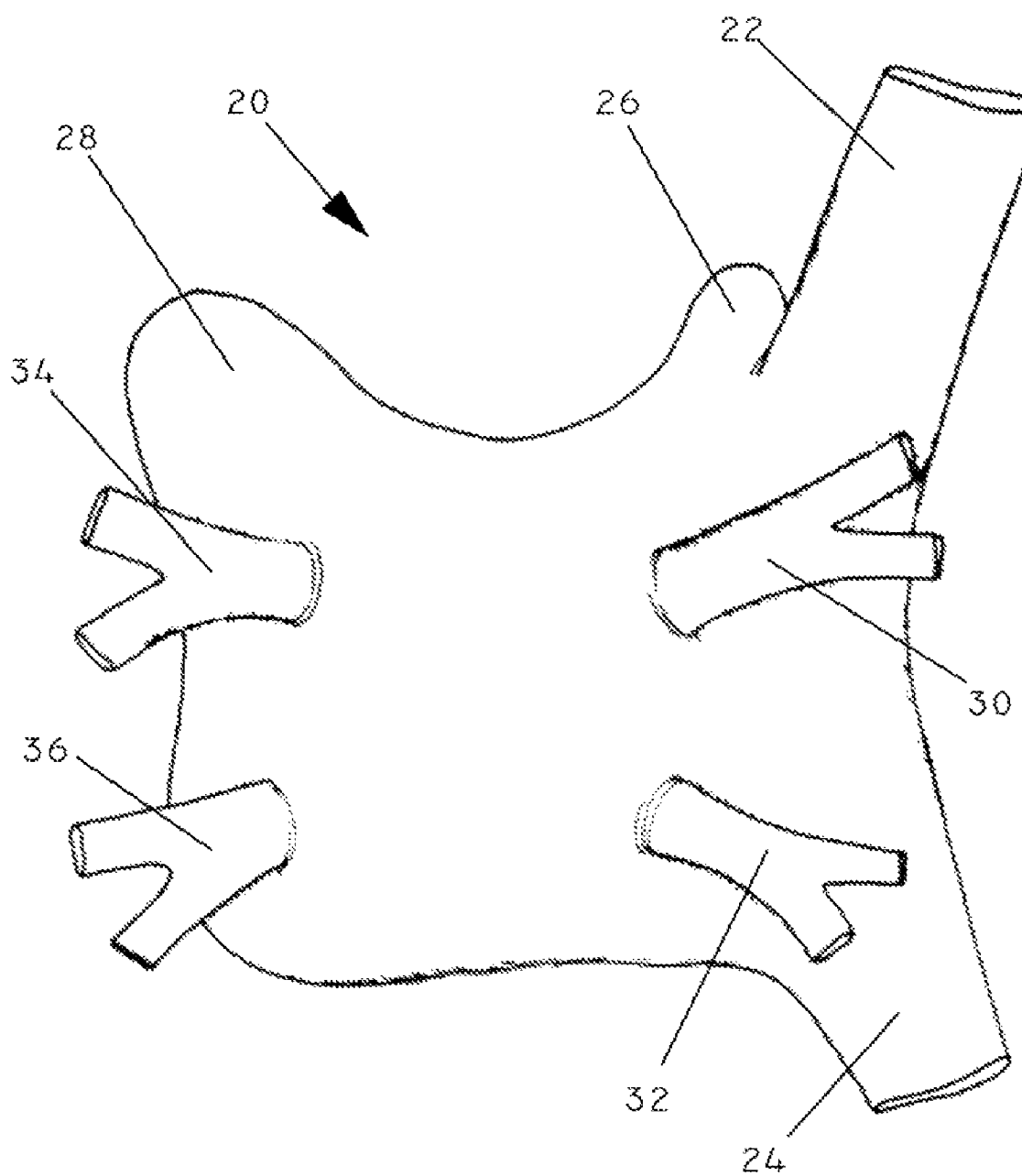
FIG. 1 is a simplified posterior view of a human heart.

While the invention may be modified in many ways, specifics have been shown by way of example in the drawings and will be described in detail. It should be understood, however, that the intention is not to limit the invention to the particular embodiments described. On the contrary, the intention is to cover all modifications, equivalents, and alternatives following within the scope and spirit of the invention as defined by the claims.

DETAILED DESCRIPTION OF THE INVENTION

In the human heart, the sinoatrial node (SA node) is a small region in the right atrial wall near the opening of the superior vena cava. The SA node is made of cells with autorhythmic characteristics, such that they are capable of initiating an action potential. Although other cardiac cells have autorhythmic characteristics, the SA node typically has the fastest rate of autorhythmicity and therefore generally controls the pacing rate of the heart. In a normal heart, an action potential originating in the SA node spreads through both atria through mechanisms including from cell to cell by gap junctions. The presence of the action potential in the myocardial cells of the atria causes the atria to contract, causing an atrial beat. The action potential is also received at the atrioventricular node (AV node), located at the base of the right atrium near the septum. Action potentials are conducted relatively slowly through the AV node before being conducted through the His bundle and the ventricular myocardium via the Purkinje fibers causing the ventricles to contract. The delay in the transmission through the AV node allows for a delay between contractions of the atria and the ventricles, resulting in adequate ventricular filling and efficient pumping.

The human heart contains an intrinsic neural network that provides local, independent heart rhythm control. This intrinsic neural network includes large numbers of intrinsic cardiac neurons associated with ganglionated plexuses (plexi) in human atrial and ventricular tissues. Specifically, human intrinsic cardiac ganglia and their associated nerves, which are found primarily embedded in epicardial fat, form multiple atrial and ventricular ganglionated plexi. In healthy patients, the intrinsic neural network of the heart helps to provide rhythm control.

However, various conditions can adversely affect the heart's rhythm. By way of example, atrial fibrillation is a condition that can adversely affect filling of the ventricles and the pumping efficiency of the heart. Atrial fibrillation is characterized by rapid, irregular, and uncoordinated depolarizations of the atria. This may result both in discomfort to a patient and an inability to undertake physical activity without excessive fatigue. In addition to causing discomfort for patients and potentially limiting physical activity, atrial fibrillation can pose a serious health risk. This is because atrial fibrillation allows blood to stagnate inside of the heart, potentially leading to the formation of blood clots. Blood clots in the vasculature are dangerous and can result in a myocardial infarction if lodged in the coronary artery or a stroke if lodged in an artery that supplies blood to the brain.

FIG. 1 shows a posterior view illustration of a typical human heart 20. The heart 20 includes the right atrium 26 and the left atrium 28. Deoxygenated blood returning to the heart passes into the heart's right atrium 26 after passing through either the superior vena cava 22 or the inferior vena cava 24. There are four pulmonary veins (30, 32, 34, and 36) that return oxygenated blood from the lungs to the left atrium 28 of the heart. These pulmonary veins include the right superior pulmonary vein 30, right inferior pulmonary vein 32, left superior pulmonary vein 34, and left inferior pulmonary vein 36.

Figure 2:
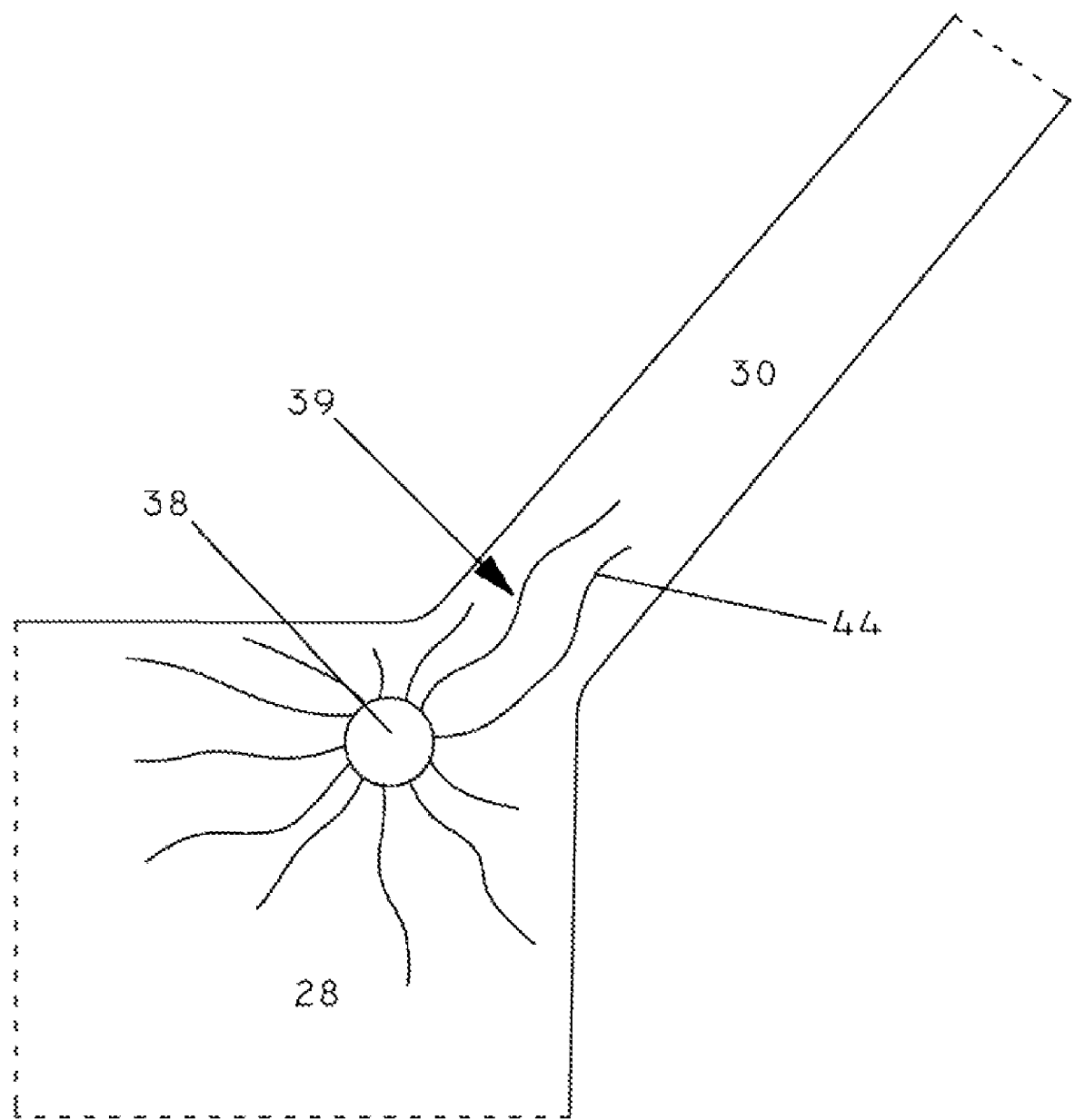
FIG. 2 is a schematic representation of a ganglionated plexus at the junction of a pulmonary vein and an atrium.

Referring now to FIG. 2, a schematic view is shown of the junction of a pulmonary vein and an atrium. Although FIG. 2 could represent any of four such junctions, for ease of description FIG. 2 is labeled to show the junction of right superior pulmonary vein 30 with left atrium 28. Near the junction is a ganglionated plexus 38. Ganglionated plexus 38 includes a plurality of neuronal axons 39. Some of these axons, such as axon 44, innervate the right superior pulmonary vein 30. Similarly, axons from other ganglionated plexi can innervate other pulmonary veins.

While not intending to be bound by theory, the ganglionated plexi (GP) are believed to play a role in the development of atrial fibrillation. The ganglionated plexi contain both parasympathetic and sympathetic neurons. As such, the ganglionated plexi can transmit signals through both parasympathetic and sympathetic nervous tissue resulting in the release of both parasympathetic and sympathetic neurotransmitters. Parasympathetic neurotransmitters can shorten the refractory period of tissue. Sympathetic neurotransmitters can increase the magnitude and duration of calcium ion transients. The combination of both parasympathetic and sympathetic neurotransmitters can cause hyperactive electrical activity, such as early after depolarizations, in tissues near where the neurotransmitters are released.

Neurotransmitters released as a result of activity in the ganglionated plexi can affect the myocardial sleeves. A myocardial sleeve is an extension of atrial myocardial tissue over the pulmonary and caval veins of the human heart. The myocardial sleeves are generally thicker at the venoatrial junctions, thinning out or disappearing as the veins divide into segmental branches. The myocardial tissue of the myocardial sleeves interconnects with myocardial tissue in the atriums of the heart. Because of this interconnection, hyperactive electrical activity in myocardial sleeves, such as in the pulmonary vein myocardial sleeves, can propagate into the myocardial tissue of the atrium via conduction of electrical signals over gap junctions between individual myocytes. Once transmitted into the myocardial tissue of the atrium, this hyperactive electrical activity can contribute to abnormal atrial rhythm, including atrial fibrillation.

One approach to preventing or treating atrial fibrillation is to prevent or mitigate the effects that the ganglionated plexi have on tissue, such as the myocardial sleeves, near the junctions between the pulmonary veins and the left atrium (venoatrial junctions). For example, signals passing through axons of both sympathetic and parasympathetic neurons (nervous tissue) innervating the pulmonary veins can be blocked thereby preventing or reducing the release of neurotransmitters near the pulmonary vein myocardial sleeves that might otherwise lead to electrical hyperactivity. In an embodiment, the invention includes a method of treating and/or preventing atrial fibrillation including applying an oscillating electrical stimulus to nervous tissue interconnecting a ganglionated plexus and a pulmonary vein, the oscillating electrical stimulus being sufficient to block transmission of electrical signals through the nervous tissue.

Another approach to preventing or treating atrial fibrillation is to prevent or block the transmission of electrical hyperactivity through myocardial tissue interconnecting the pulmonary vein myocardial sleeves and the myocardial tissue of the atrium. In an embodiment, the invention includes a method of treating and/or preventing atrial fibrillation including applying an oscillating electrical stimulus to myocardial tissue interconnecting a pulmonary vein myocardial sleeve and the myocardial tissue of an atrium, the oscillating electrical stimulus sufficient to block transmission of electrical signals through the myocardial tissue.

Hyperactivity of the ganglionated plexi may be mediated by input to the ganglionated plexi from the autonomic nervous system. The ganglionated plexi can receive input from the autonomic nervous system through nervous tissue located in the region of the junction between the pulmonary veins and the left atrium. As such, another approach to preventing and/or treating atrial fibrillation is to block the transmission of signals through nervous tissue interconnecting the autonomic nervous system with the ganglionated plexi. In an embodiment, the invention includes a method of treating and/or preventing atrial fibrillation including applying an oscillating electrical stimulus to nervous tissue interconnecting a ganglionated plexus and the autonomic nervous system, the oscillating electrical stimulus sufficient to block transmission of electrical signals through the nervous tissue.

Figure 3:
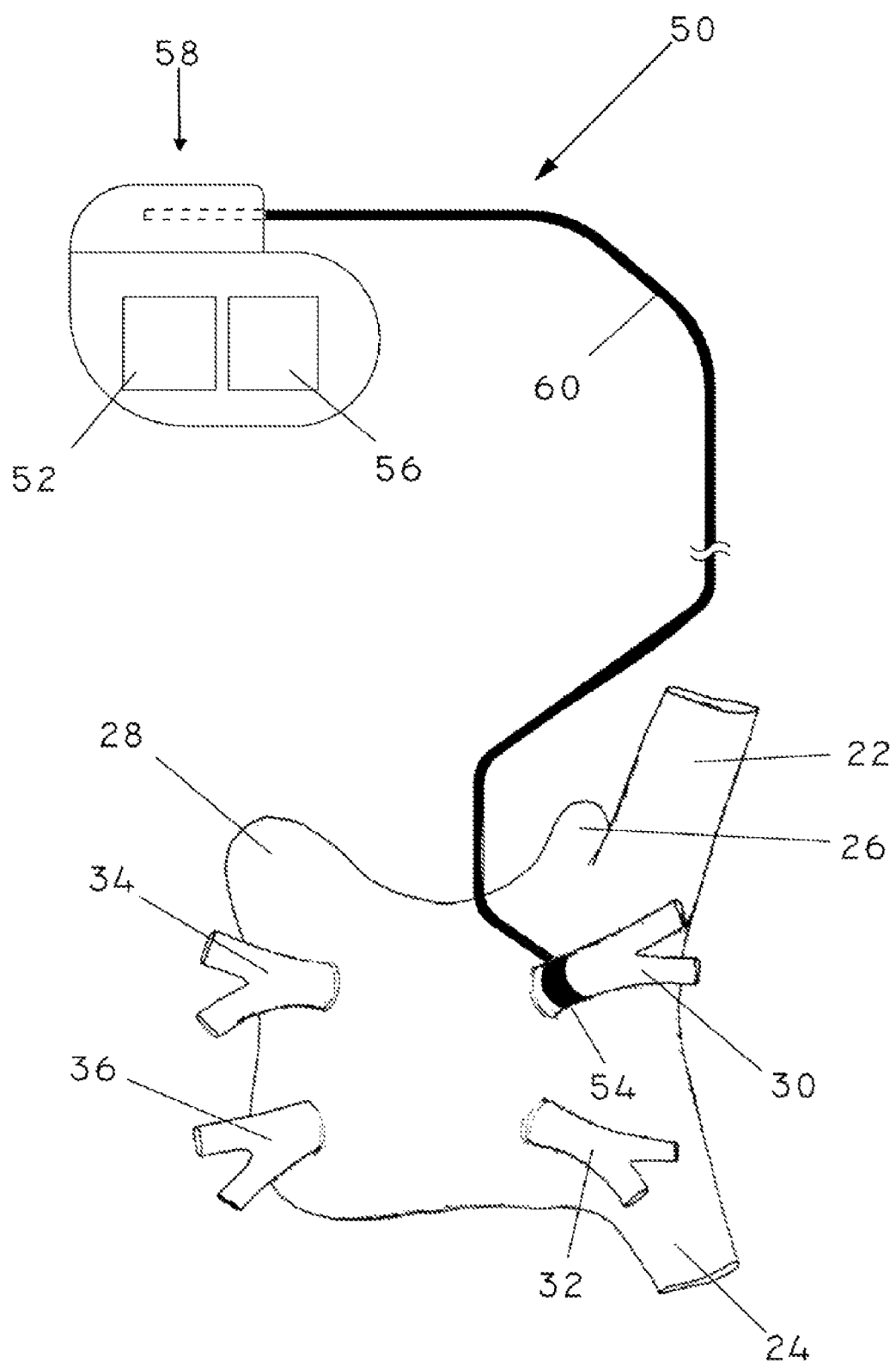
FIG. 3 is a schematic view of an implantable medical device in accordance with an embodiment of the invention.

An implantable medical device 50, in accordance with an embodiment of the invention is shown in FIG. 3. Implantable medical device 50 includes a stimulation generator 58 configured to generate an oscillating electrical stimulus. Implantable medical device 50 further includes an electrode cuff 54 configured to deliver the electrical stimulus to target tissues. Electrode cuff 54 is in communication with stimulation generator 58 via stimulation lead 60. However, in some embodiments, the electrode cuff can be in wireless communication with the stimulation generator 58. Electrode cuff 54 can also be used to sense electrical activity in the adjacent tissue. In some embodiments, the electrode cuff 54 is configured to surround a tissue site, such as a pulmonary vein. In the embodiment of FIG. 3, electrode cuff 54 surrounds the right superior pulmonary vein 30, at or near the junction between the right superior pulmonary vein 30 and the left atrium 28.

The electrode cuff can be positioned so that is disposed over the myocardial sleeve within the pulmonary vein. In some embodiments, an electrode cuff is positioned on or around a pulmonary vein less than or equal to about 5 cm away from the junction between that pulmonary vein and the left atrium. In some embodiments, an electrode cuff is positioned on or around a pulmonary vein less than or equal to about 2 cm away from the junction between that pulmonary vein and the left atrium. In some embodiments, an electrode cuff is positioned on or around a pulmonary vein less than or equal to about 1 cm away from the junction between that pulmonary vein and the left atrium.

The stimulation generator 58 can include control circuitry 56 and stimulation circuitry 52. In some embodiments, both control circuitry 56 and stimulation circuitry 52 are disposed together within a common housing. In other embodiments, control circuitry 56 and stimulation circuitry 52 are disposed separately from one another. The control circuitry 56 can be configured to control parameters of the stimulation provided by the stimulation generator 58. It will be appreciated that the stimulation generator 58 can include components such as a power source, memory circuitry, communications circuitry, a microprocessor, and the like.

The oscillating electrical stimulus passes through electrode cuff 54 and into the adjacent tissue, which can include nervous tissue and myocardial tissue. In some embodiments, an oscillating electrical stimulus can be delivered by the electrode cuff 54 to nervous tissue that is sufficient to block the transmission of electrical signals through the nervous tissue. In some embodiments, an oscillating electrical stimulus can be delivered by the electrode cuff 54 to nervous tissue that is sufficient to keep the nervous tissue in a refractory state. In some embodiments, an oscillating electrical stimulus can be delivered by the electrode cuff 54 to nervous tissue that is sufficient to block the transmission of electrical signals through the tissue, but is below the excitatory threshold of the tissue.

In some embodiments, an oscillating electrical stimulus can be delivered by the electrode cuff 54 to myocardial tissue that is sufficient to block the transmission of electrical signals between myocytes. In some embodiments, an oscillating electrical stimulus can be delivered by the electrode cuff 54 to myocardial tissue that is sufficient to keep the myocardial tissue in a refractory state. In some embodiments, an oscillating electrical stimulus can be delivered by the electrode cuff 54 to myocardial tissue that is sufficient to block the transmission of electrical signals the tissue, but is below the excitatory threshold of the tissue.

The oscillating electrical stimulus can include an oscillating electrical potential (voltage) and/or an oscillating electrical current. The applied electrical stimulus can create a reversible block of depolarization waves such that after the electrical stimulus is removed, the transmission of depolarization waves can resume.

It will be appreciated that the specific parameters of the applied electrical stimulus, including the frequency, amplitude, waveform, etc., can vary based on factors including the proximity of the electrode(s) to the targeted tissue, the number of electrodes used to stimulate the tissue, the type of tissue stimulated, and the like. However, in some embodiments, the applied electrical stimulus can have a high frequency. In an embodiment, the electrical stimulus can have a frequency of about 1 kHz to about 30 kHz. In an embodiment, the electrical stimulus can have a frequency of about 2 kHz to about 20 kHz. In some embodiments, the electrical stimulus has a frequency of about 3 kHz to about 5 kHz.

The waveform of the applied electrical stimulus may take on various forms. By way of example, the waveform can include a sinusoidal wave, a square wave, a rectangular wave, a triangular wave, a stair-step wave, or the like. The waveform of the applied electrical stimulus can be monophasic or biphasic. In the context of an applied electrical current, biphasic waveforms deliver current that first flows in a positive direction for a specific duration and then reverses the direction of current so that it flows in a negative direction for a specific duration. While not intending to be bound by theory, it is believed that biphasic electrical stimuli are more effective at blocking the transmission of depolarization waves through tissue than are monophasic electrical stimuli.

It will be appreciated that the amplitude of the stimulus will vary depending on factors such as the proximity of the electrode(s) to the targeted tissue, the number of electrodes used to stimulate the tissue, the type of tissue stimulated, and the like. However, in some embodiments, the amplitude of the stimulus can be greater than or equal to about 2.0 Volts peak to peak (or 2.0 $V_{P-P}$). In some embodiments, the amplitude of the stimulus can be greater than or equal to about 2.4 $V_{P-P}$. In some embodiments, the amplitude of the stimulus can be greater than or equal to about 3.0 $V_{P-P}$.

In some embodiments, the amplitude of the stimulus can be greater than or equal to about 0.1 milliamps peak to peak (or 0.1 $mA_{P-P}$). In some embodiments, the amplitude of the stimulus can be greater than or equal to about 0.2 $mA_{P-P}$. In some embodiments, the amplitude of the stimulus can be greater than or equal to about 0.3 $mA_{P-P}$.

The electrical stimulus can be applied for a period of time effective to treat or prevent atrial fibrillation. In some embodiments the electrical stimulus is applied for a period of time representing the expected duration of the atrial fibrillation event. In some embodiments, the electrical stimulus is applied for a length of time approximately equal to the time for a contraction cycle of the heart. In some embodiments, the electrical stimulus is applied for at least about one second. In some embodiments, the electrical stimulus is applied for at least about five minutes. In some embodiments, the electrical stimulus is applied for a period of time and then stopped, after which the heart is monitored for signals that can indicate recurrence of atrial fibrillation. In some embodiments, the electrical stimulus is applied continuously for a period of time lasting days, weeks, or even months.

In some embodiments, the electrical stimulus includes relatively long, low amplitude hyperpolarizing anodal stimulation. In some embodiments, the low amplitude stimulation is applied for a period of time between about 2 and about 4 milliseconds. In some embodiments, this relatively long low amplitude stimulation is followed by high frequency sinusoidal stimulation.

The electrical stimulus can be commenced when desirable. In some embodiments, the electrical stimulus is commenced during the atrial refractory period so as to reduce the likelihood of inadvertently initiating an abnormal atrial rhythm. In some embodiments, the electrical stimulus is commenced when a patient is predicted to be at an elevated risk of developing atrial fibrillation. By way of example, a patient may be at an elevated risk of developing atrial fibrillation after a defibrillation shock is delivered to the heart by an implantable medical device such as an implantable cardioverter-defibrillator (ICD). Therefore, in some embodiments the electrical stimulation can be commenced after a defibrillation shock is delivered to the heart by an ICD or a similar device. In some embodiments, the electrical stimulus is commenced within about 100 milliseconds after a sensed atrial contraction.

Figure 4:
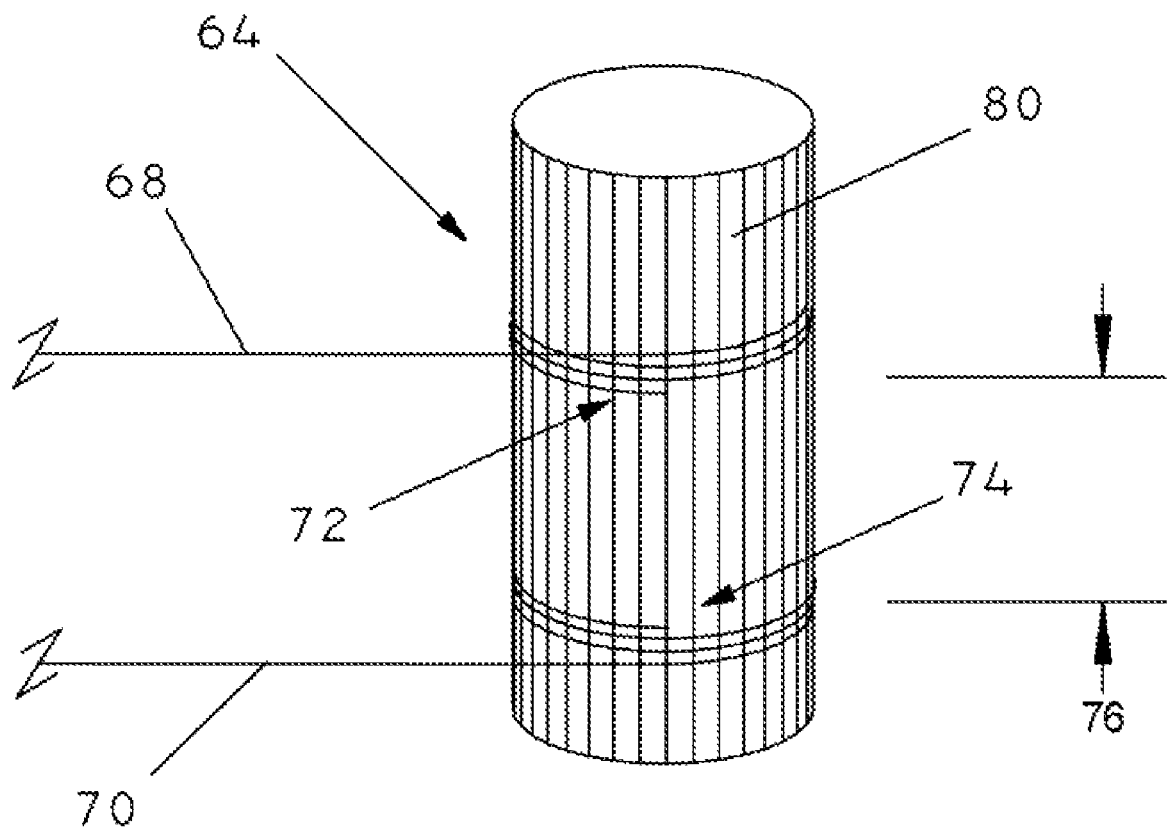
FIG. 4 is a schematic view of a bipolar electrode cuff in accordance with an embodiment of the invention.

In some embodiments, the electrode cuff can be unipolar or bipolar. Referring now to FIG. 4, a schematic view of a bipolar electrode cuff 64 is shown interfacing with a section of tissue 80. The tissue 80 can be a pulmonary vein or another physiological structure such as the superior vena cava. The electrode cuff 64 includes a first conductor 68 and a second conductor 70. The first and second conductors (68, 70) can be formed of, or include, a conductive material, such as a noble metal. An exemplary conductive material is platinum. The first conductor 68 is wrapped around the tissue 80 forming a first electrode 72. Similarly, the second conductor 70 is wrapped around the tissue 80 forming a second electrode 74. In other embodiments, the first conductor 68 and the second conductor 70 are adjacent to the tissue 80, but not wrapped around the tissue 80. The distance 76 between the first electrode 72 and the second electrode 74 can vary depending on factors such as the parameters of the stimulus to be delivered and the tissue being stimulated, amongst other factors. In some embodiments, the distance 76 between the first electrode 72 and the second electrode 74 is from about 1 mm to about 4 cm. In some embodiments, more than two electrodes can be used. For example, in some embodiments, three electrodes are used.

While the embodiment of FIG. 3 includes an electrode cuff 54 at the junction between the right superior pulmonary vein 30 and the right atrium 26, it will be appreciated that the electrode cuffs can be disposed at other tissue sites. For example, an electrode cuff can be disposed at any junction between a pulmonary vein and the left atrium or at the junction between the superior vena cava and the right atrium. In addition, in some embodiments, multiple electrode cuffs can be used in order to deliver an electrical stimulus to multiple tissue sites. In some cases, the electrode can also be positioned endocardially adjacent to the coronary sinus, the posterior right atrium, the pulmonary artery, or a pulmonary vein.

Figure 5:
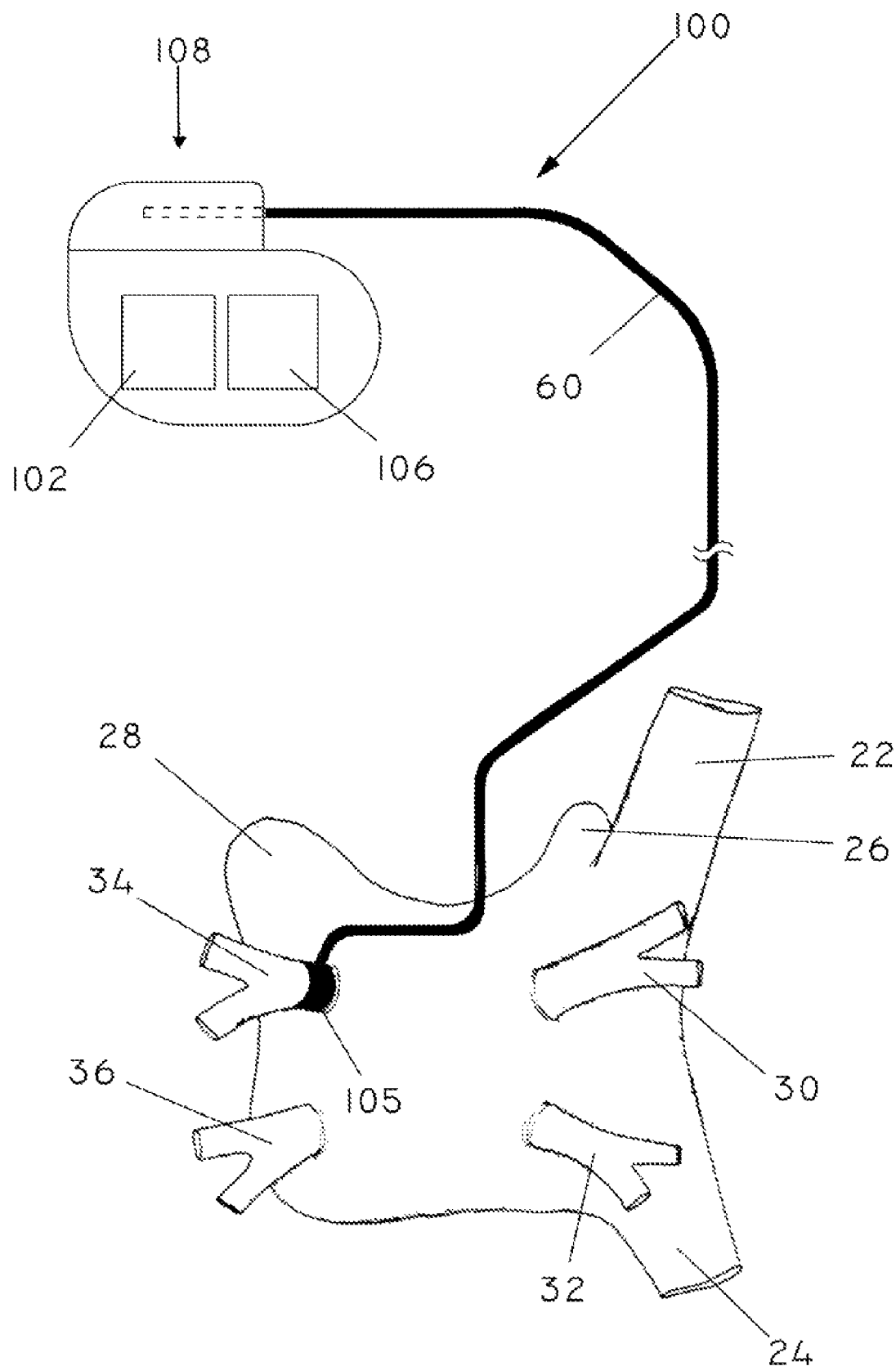
FIG. 5 is a schematic view of an implantable medical device in accordance with another embodiment of the invention.

An implantable medical device 100, in accordance with another embodiment of the invention, is shown in FIG. 5. Implantable medical device 100 includes a stimulation generator 108 configured to generate an oscillating electrical stimulus. The stimulation generator 108 can include control circuitry 106 and stimulation circuitry 102. Implantable medical device 100 further includes an electrode cuff 105 configured to deliver the electrical stimulus to target tissues. Electrode cuff 105 is in communication with stimulation generator 108 via stimulation lead 110. In this embodiment, electrode cuff 105 surrounds the left superior pulmonary vein 34, at or near the junction between the left superior pulmonary vein 34 and the left atrium 28.

Figure 6:
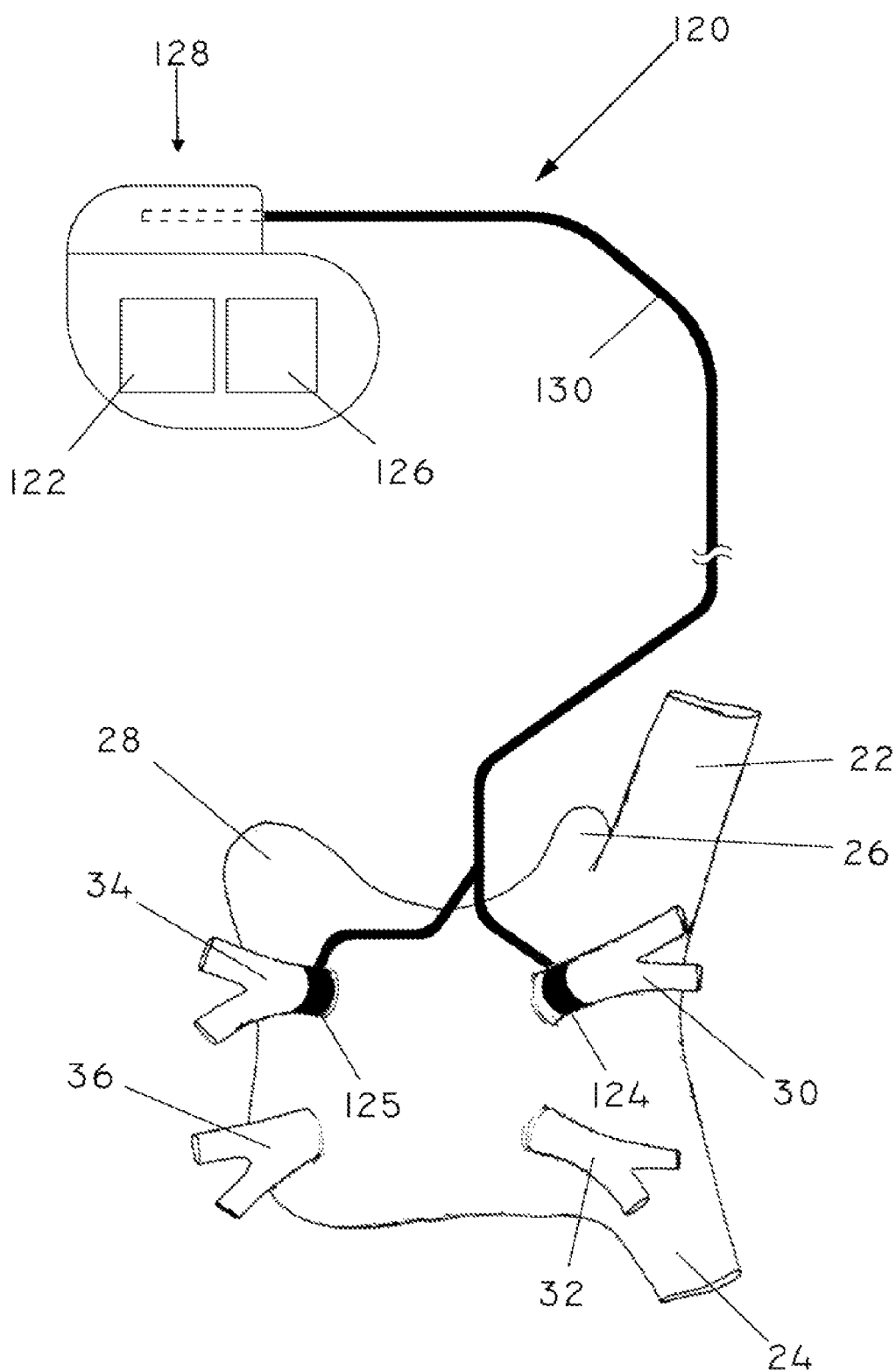
FIG. 6 is a schematic view of an implantable medical device in accordance with another embodiment of the invention.

An implantable medical device 120, in accordance with another embodiment of the invention is shown in FIG. 6. Implantable medical device 120 includes a stimulation generator 128 configured to generate an oscillating electrical stimulus. The stimulation generator 128 can include control circuitry 126 and stimulation circuitry 122. Implantable medical device 120 includes a first electrode cuff 124 and a second electrode cuff 125 configured to deliver an electrical stimulus to target tissues. First electrode cuff 124 is in communication with stimulation generator 128 via stimulation lead 120. Second electrode cuff 125 is also in communication with stimulation generator 128 via stimulation lead 120. In this embodiment, first electrode cuff 124 surrounds the right superior pulmonary vein 30, at the junction between the right superior pulmonary vein 30 and the left atrium 28. Second electrode cuff 125 surrounds the left superior pulmonary vein 34, at the junction between the left superior pulmonary vein 34 and the left atrium 28.

The stimulation lead can be in communication with multiple electrodes and can include a single conductive path such that multiple electrodes each deliver the same stimulus. Alternatively, multiple stimulation leads can be used for multiple electrodes, or a stimulation lead including multiple isolated conductive paths can be used such that the stimulation parameters for each electrode can be selected separately.

In some embodiments, the implantable medical device can be configured to selectively apply the electrical stimulus to block transmission of depolarization waves in the subject tissue. While not intending to be bound by theory, selectively blocking transmission of depolarization waves, in contrast to continuously blocking transmission of depolarization waves, can offer advantages in the context of implantable medical devices. For example, selectively applying the electrical stimulus can allow the battery life of the implantable medical device to be maximized. In an embodiment, the implantable medical device can monitor the physiological state of the patient and then deliver the electrical stimulus to the target tissue when atrial fibrillation is occurring or when conditions indicate that atrial fibrillation is imminent.

For example, in some embodiments, the implantable medical device can monitor the intrinsic electrical activity of the heart, including the atria, and then apply an electrical stimulus to block transmission of depolarization waves and thus terminate atrial fibrillation when an indicator of atrial fibrillation, such as premature atrial contraction (PAC), is detected. The implantable medical device can include sensing circuitry to process signals from a sensor. For example, the sensing circuitry can process a sensor signal in order to identify events, such as premature atrial contractions (PACs). The sensing circuitry can include an amplifier that amplifies signals, such as atrial electrocardiograms.

Figure 7:
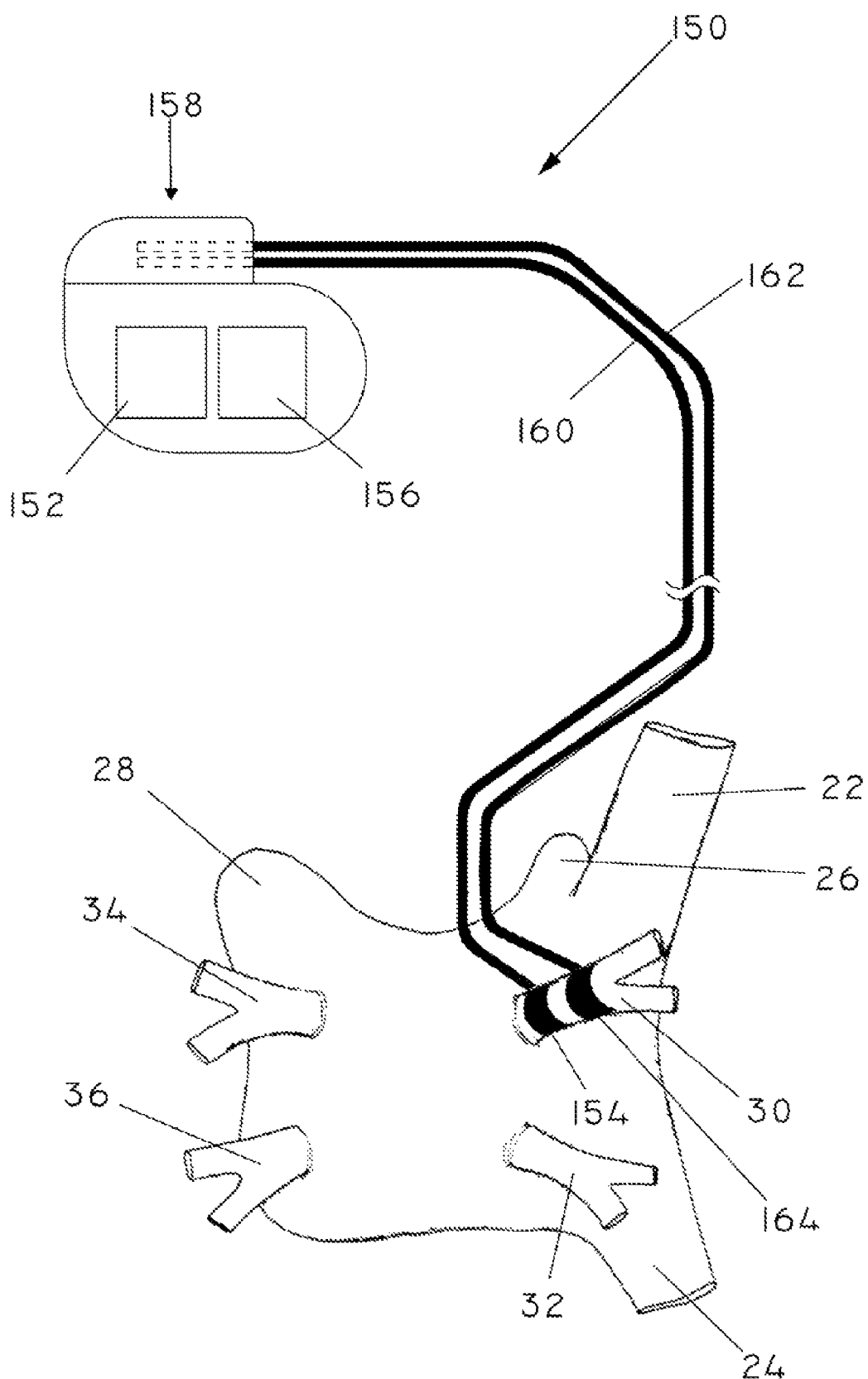
FIG. 7 is a schematic view of an implantable medical device in accordance with another embodiment of the invention.

In some embodiments, the implantable medical device includes a sensor that can be attached to a tissue site that detects depolarization waves that may lead to atrial fibrillation. For example a sensor can be attached to a ganglionated plexus or a pulmonary vein. Referring now to FIG. 7, an embodiment of an implantable medical device 150 is shown including a sensor for detecting depolarization waves in a target tissue. Implantable medical device 150 includes a stimulation generator 158 configured to deliver an oscillating electrical stimulus. The stimulation generator 158 can include control circuitry 156 and stimulation circuitry 152. The control circuitry 156 can be configured to provide for selective delivery of stimulation from the stimulation generator 158. Implantable medical device 150 further includes a stimulation cuff 154 configured to deliver the electrical stimulus. Stimulation cuff 154 is in communication with stimulation generator 158 via stimulation lead 160. As shown in the embodiment of FIG. 7, stimulation cuff 154 surrounds the right superior pulmonary vein 30, at the junction between the right superior pulmonary vein 30 and the left atrium 28. However, in other embodiments, the stimulation cuff 154 is disposed at or near a different junction between a pulmonary vein and the left atrium or near the junction between the superior vena cava and the right atrium.

A sensor cuff 164 engages the target tissue, in this case the right superior pulmonary vein 30. The control circuitry 156 can be in electrical communication with the sensor cuff 164 via sensor lead 162. The control circuitry 156 can include sensing circuitry to process signals from the sensor cuff 164. When the sensor cuff 164 detects depolarization waves that are indicative of atrial fibrillation or that indicate atrial fibrillation is likely, the control circuitry 156 can cause an electrical stimulus to be delivered from the stimulation circuitry 152 to the target tissue through stimulation cuff 154. It will be appreciated that in some embodiments the same electrode used to deliver an electrical stimulus can be used as a sensor to detect electrical activity.

Figure 8:
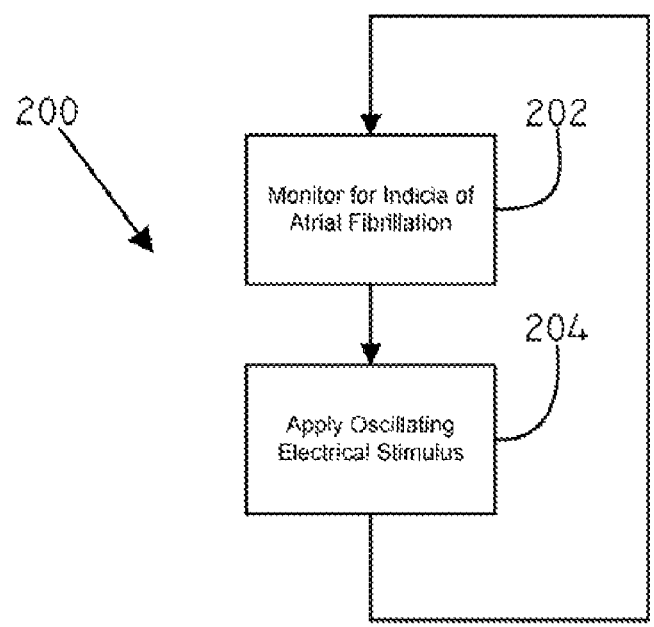
FIG. 8 is a flow chart illustrating steps of a method for treating atrial fibrillation.

Embodiments of the invention can include methods of treating atrial fibrillation. An example of a method 200 for treating atrial fibrillation is depicted in FIG. 8. The method 200 includes the step 202 of monitoring the patient for indicia of atrial fibrillation. Indicia of atrial fibrillation can include sensed electrical activity consistent with atrial fibrillation such as rapid and irregular timing of sensed atrial activations, rapid and irregular timing of sensed ventricular activations, rapid atrial activations with dissociated timing relative to ventricular activations, a pattern of depolarization waves consistent with atrial fibrillation, a loss of atrial contractility, changes in heart sounds consistent with atrial fibrillation, a reduction in the velocity of blood leaving the atria, and the like.

The method of FIG. 8 can also include the step 204 of applying an oscillating electrical stimulus to a tissue of the patient, such as the pulmonary vein, when indicia of atrial fibrillation are detected. This oscillating electrical stimulus is configured to be effective to block transmission of electrical signals through a targeted tissue, such as nervous tissue or myocardial tissue. The parameters of the oscillating electrical stimulus, such as the frequency, waveform, amplitude, and duration can be as described above. In some embodiments of method 200, the oscillating electrical stimulus is applied to a junction between the pulmonary vein and a left atrium of the patient and/or to a pulmonary vein myocardial sleeve.

Figure 9:
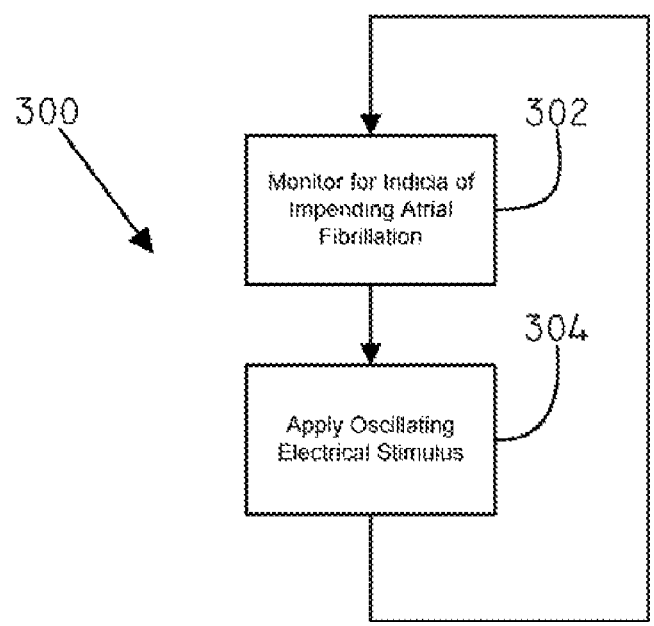
FIG. 9 is a flow chart illustrating steps of a method for preventing atrial fibrillation.

Embodiments of the invention can also include methods of preventing atrial fibrillation. Referring now to FIG. 9, a flow chart of a method of preventing atrial fibrillation is shown. The method 300 includes the step 302 of monitoring for indicia of impending atrial fibrillation. Indicia of impending atrial fibrillation can include a signal representative of hyperactivity of a ganglionated plexus, periods of atrial excitability characterized by premature atrial contractions, short runs of atrial tachycardia, particular R-R intervals, and the like.

The method 300 can also include the step 304 of applying an oscillating electrical stimulus to a tissue of a patient when indicia of impending atrial fibrillation are detected. This oscillating electrical stimulus can be configured to block transmission of electrical signals through a tissue of a patient, such as nervous tissue and/or myocardial tissue. The parameters of the oscillating electrical stimulus, such as the frequency, waveform, amplitude, and duration can be as described above. In some embodiments of method 300, the oscillating electrical stimulus is applied to a junction between the pulmonary vein and a left atrium of the patient and/or to a pulmonary vein myocardial sleeve.

In some embodiments, an electrical neurogram associated with atrial fibrillation can be recorded for an individual patient and then later applied to identify circumstances where atrial fibrillation is likely. As such, in some embodiments, the method can include a step of identifying a neurogram pattern that indicates that atrial fibrillation is likely, monitoring for the occurrence of such patterns, and then applying an oscillating electrical stimulus to prevent atrial fibrillation from occurring. The neurogram can reflect the electrical activity of nervous tissue at a site of interest such as on or near an atrium, on or near a pulmonary vein, on or near the superior or inferior vena cava, and the like.

Figure 10:
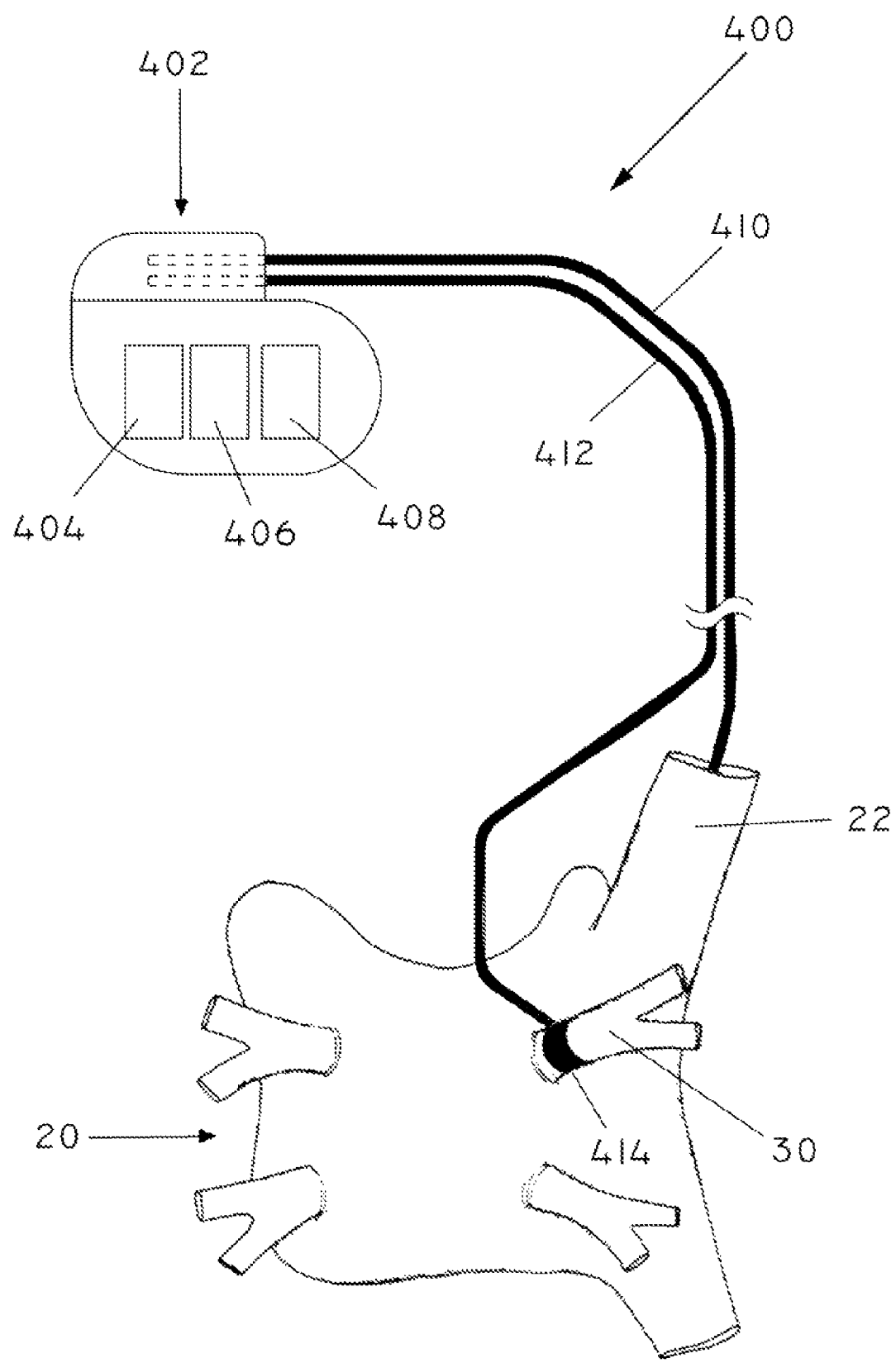
FIG. 10 is a schematic view of an implantable cardiac rhythm management (CRM) device including features for providing therapy for atrial fibrillation in accordance with another embodiment of the invention.

In some embodiments, features as described herein can be incorporated with an implantable cardiac rhythm management (CRM) device, such as a pacemaker, a cardiac resynchronization therapy (CRT) device, a remodeling control therapy (RCT) device, an implantable cardioverter/defibrillator, or a pacemaker-cardioverter/defibrillator. Referring now to FIG. 10, a schematic view of an implantable CRM device 400 is shown in accordance with an embodiment of the invention. The implantable CRM device includes a pulse generator 402. The pulse generator 402 can include control circuitry 404, pacing circuitry 406, and electrical stimulation circuitry 408. The device can include a pacing lead 410 in communication with the pulse generator. The pacing lead 410 passes into the heart 20 through the superior vena cava 22. The pacing lead 410 provides electrical communication between the pulse generator 402 and one or more pacing electrodes (not shown) disposed within one or more chambers of the heart 20. The pulse generator 402 can deliver pacing pulses to the heart 20 in order maintain a desirable heart rate. In some embodiments, the pulse generator 402 can deliver defibrillation shocks to the heart 20. The implantable CRM device 400 also includes a stimulation lead 412 in communication with the pulse generator 402 and a stimulation cuff 414 disposed around the right superior pulmonary vein 30. The pulse generator 402 can deliver electrical stimuli to the pulmonary vein sufficient to block transmission of electrical signals through nervous tissue and/or myocardial tissue in order to treat and/or prevent atrial fibrillation.

It will be appreciated that the implantable CRM device 400 can also include other features associated with cardiac rhythm management devices. For example, the implantable CRM device 400 can include features described in U.S. Pat. No. 6,928,325, the contents of which are herein incorporated by reference.

Figure 11:
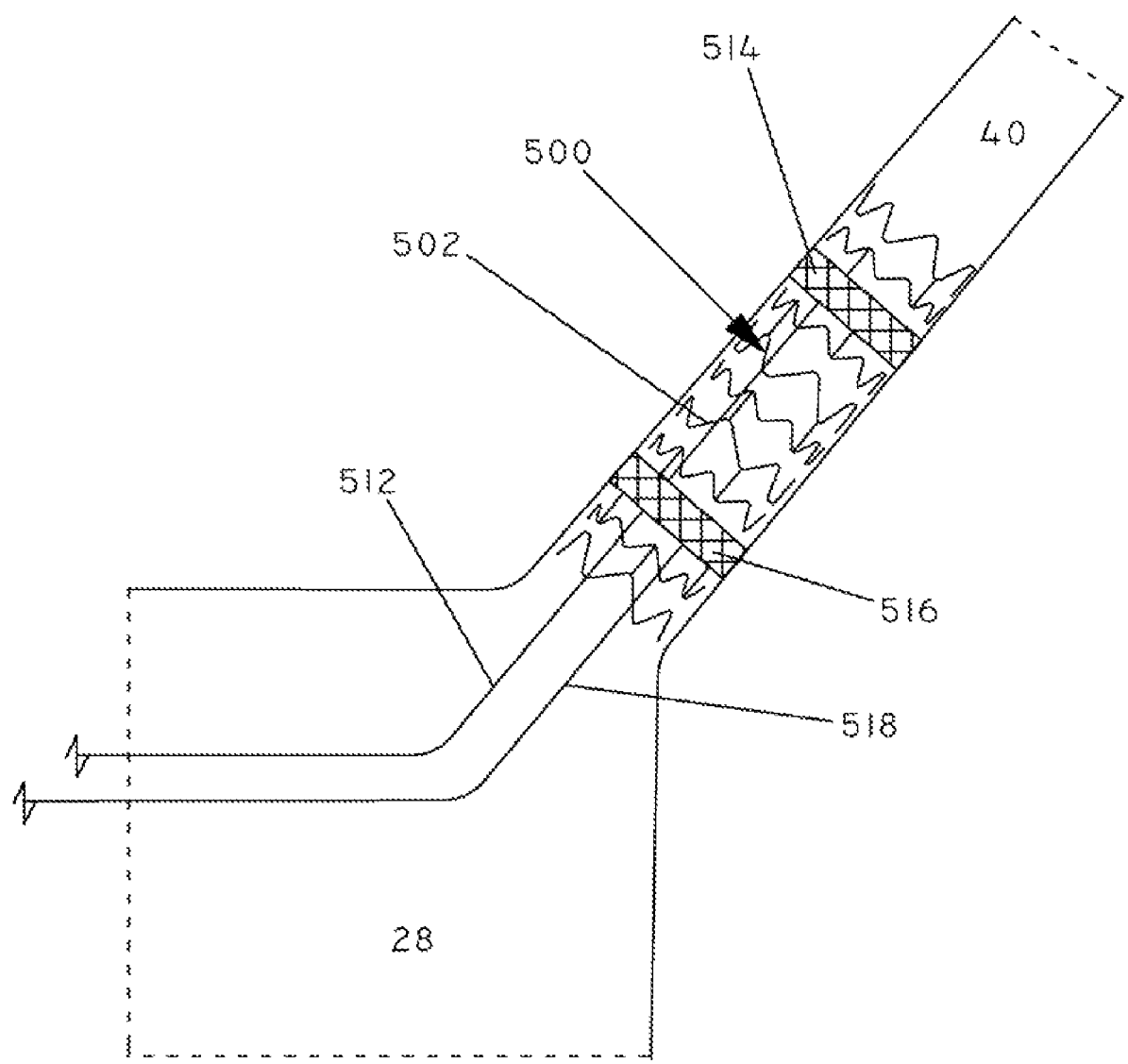
FIG. 11 is a schematic view of an endovascular device for providing therapy to treat atrial fibrillation in accordance with another embodiment of the invention.

FIG. 11 is a schematic view of an endovascular device 500 for providing therapy to treat atrial fibrillation in accordance with another embodiment of the invention. The endovascular device 500 can be disposed within a pulmonary vein 40 (any of the right superior pulmonary vein, the right inferior pulmonary vein, the left superior pulmonary vein, and the left inferior pulmonary vein) and adjacent to the intersection of the pulmonary vein 40 and the left atrium 28. The endovascular device 500 can assume a first diameter which is relatively narrow for facilitation of the percutaneous insertion and positioning of the endovascular device 500. The endovascular device 500 can also assume a second diameter which is larger than the first diameter that can be large enough to engage the inner walls of the vascular lumen in which the endovascular device 500 is deployed. The endovascular device 500 can be self-expanding and/or balloon expandable. The endovascular device 500 can include a stent. Various features of stents are described in U.S. Pat. No. 7,081,130, the contents of which is herein incorporated by reference.

In some embodiments, the endovascular device can include a plurality of struts or wires 502. The struts can be made of a polymer, metal, or ceramic material that is biocompatible. The endovascular device 500 can also include one or more electrodes. In this embodiment, the endovascular device 500 includes a first electrode 514 and a second electrode 516. The first electrode 514 and the second electrode 516 can be positioned in contact with the inner wall of the vascular lumen. A first conductor 512 can be in electrical communication with the first electrode 514 and a second conductor 514 can be in electrical communication with the second electrode 516. The first conductor 512 and the second conductor 514 can be connected to a device for generating an oscillating electrical stimulus that is then delivered to tissue such as nervous tissue and/or myocardial tissue through the first conductor 512 and/or the second conductor 514.

Electrodes used to deliver an oscillating electrical stimulus can be configured for endocardial placement. For example, electrodes can include a fixation mechanism such as an active or passive fixation mechanism to aid in attaching the electrode to a tissue site. The fixation mechanism can include aspects such as screw-in fixation element.

In some embodiments, electrodes used to deliver an oscillating electrical stimulus are untethered. For example, the electrodes can be in wireless communication with another component, such as a device for generating a control signal.

The present invention should not be considered limited to the particular embodiments described above, but rather should be understood to cover all aspects of the invention as fairly set out in the attached claims. Various modifications, equivalent processes, as well as numerous structures to which the present invention may be applicable will be readily apparent to those of skill in the art to which the present invention is directed upon review of the present specification. The claims are intended to cover such modifications and devices.

The above specification provides a complete description of the structure and use of the invention. Since many of the embodiments of the invention can be made without parting from the spirit and scope of the invention, the invention resides in the claims.

One of ordinary skill in the art will understand that the modules, circuitry, and methods shown and described herein with regard to various embodiments of the invention can be implemented using software, hardware, and combinations of software and hardware. As such, the illustrated and/or described modules and circuitry are intended to encompass software implementations, hardware implementations, and software and hardware implementations.

It should be noted that, as used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration. The phrase "configured" can be used interchangeably with other similar phrases such as "arranged", "arranged and configured", "constructed and arranged", "constructed", "manufactured and arranged", and the like.

What is claimed is:

1. A method of treating and/or preventing atrial fibrillation comprising:
    applying an oscillating electrical stimulus to a tissue of a patient with an implantable medical device; the oscillating electrical stimulus sufficient to block transmission of electrical signals through the tissue; the tissue adjacent to a junction between a pulmonary vein and a left atrium of the patient.

2. The method of claim 1, the tissue comprising nervous tissue.

3. The method of claim 1, the tissue comprising nervous tissue interconnecting a ganglionated plexus and a pulmonary vein.

4. The method of claim 1, the tissue comprising nervous tissue interconnecting a ganglionated plexus and an autonomic nervous system.

5. The method of claim 1, the tissue comprising myocardial tissue interconnecting a pulmonary vein myocardial sleeve and atrial myocardium.

6. The method of claim 1, the tissue comprising a superior vena cava.

7. The method of claim 1, the oscillating electrical stimulus having a frequency of about 1 kHz to about 30 kHz.

8. The method of claim 1, wherein the oscillating electrical stimulus is below the excitatory threshold of the tissue.

9. The method of claim 1, the oscillating electrical stimulus comprising a sinusoidal wave form.

10. The method of claim 1, the oscillating electrical stimulus comprising a peak potential of greater than or equal to about $2.0\,\mathrm{Vp}_{p-p}$.

11. The method of claim 1, further comprising detecting a physiological signal indicative of atrial fibrillation.

12. The method of claim 11, the physiological signal indicative of atrial fibrillation selected from the group consisting of an ECG signal consistent with atrial fibrillation, a pattern of depolarization waves consistent with atrial fibrillation, and a drop in a measure of cardiac efficiency.

13. The method of claim 1, further comprising detecting a physiological signal indicative of impending atrial fibrillation.

14. The method of claim 13, the physiological signal indicative of impending atrial fibrillation selected from the group consisting of a signal representative of hyperactivity of a ganglionated plexus and aberrant electrical activity in tissues of a pulmonary vein.

15. The method of claim 1, further comprising:
    implanting an electrode cuff on tissue adjacent to a junction between a pulmonary vein and a left atrium of a patient.

16. The method of claim 15, the tissue comprising nervous tissue.

17. The method of claim 15, the tissue comprising nervous tissue interconnecting a ganglionated plexus and a pulmonary vein.

18. The method of claim 15, the tissue comprising nervous tissue interconnecting a ganglionated plexus and an autonomic nervous system.

19. The method of claim 15, the tissue comprising myocardial tissue interconnecting a pulmonary vein myocardial sleeve and atrial myocardium.

20. The method of claim 15, the tissue comprising a superior vena cava.

* * * * *